United States Patent [19]

Asselin et al.

[11] 4,171,443

[45] Oct. 16, 1979

[54] 10b-AZAFLUORANTHENE DERIVATIVES AND PRECURSORS THEREOF

[75] Inventors: André A. Asselin, St. Laurent; Leslie G. Humber, Dollard des Ormeaux, both of Canada

[73] Assignee: Ayerst, McKenna & Harrison Limited, Montreal, Canada

[21] Appl. No.: 904,113

[22] Filed: May 8, 1978

[51] Int. Cl.$^2$ .................. C07D 491/06; C07D 495/06
[52] U.S. Cl. .................. 546/66; 260/326.12 R; 260/326.13 H; 424/256
[58] Field of Search .................. 260/293.55, 293.53; 546/66

[56] References Cited

U.S. PATENT DOCUMENTS 3,989,717  11/1976  Heath-Brown .................. 260/293.55

FOREIGN PATENT DOCUMENTS 2304729  8/1973  Fed. Rep. of Germany ...... 260/293.55

OTHER PUBLICATIONS

Bowden, B. et al., *Australian J. Chem.*, 28, 2681-2701 (1975).

*Primary Examiner*—John M. Ford
*Assistant Examiner*—Richard A. Schwartz
*Attorney, Agent, or Firm*—Arthur E. Wilfond

[57] ABSTRACT

10b-Azafluoranthene derivatives characterized by having a 1,2,3,3a,5,6-hexahydro-4-oxa(or thia)-10b-azafluoranthene nucleus having an alkanamine substituent at position 3 or 3a are disclosed. The nucleus is optionally further substituted on the aromatic ring. The derivatives are useful antidepressant agents, and methods for their preparation and use are also disclosed.

11 Claims, No Drawings

10B-AZAFLUORANTHENE DERIVATIVES AND PRECURSORS THEREOF

BACKGROUND OF THE INVENTION a. Field of the Invention

This invention relates to novel 10b-azafluoranthene derivatives and their therapeutically acceptable salts, to a process and intermediates for preparing the derivatives, to methods for using the derivatives and to compositions thereof.

More specifically, the present invention relates to novel 1,2,3,3a,5,6-hexahydro-4-oxa(or thia)-10b-azafluoranthene derivatives having an alkanamine substituent at position 3 or 3a. These derivatives are useful antidepressant agents in a mammal at dosages which do not elicit undesirable side effects. The combination of these attributes render the 1,2,3,3a,5,6-hexahydro-4-oxa(or thia)-10b-azafluoranthene derivatives of this invention therapeutically useful.

b. Description of the Prior Art

Only a limited number of compounds having an azafluoranthene nucleus are reported. An example of such a report is by B. F. Bowden et al., Aust. J. Chem., 28, 2681 (1975) wherein 3,4-diazafluoranthene and 1,6-diazafluoranthene are described.

The novel compounds of this invention have a 1,2,3,3a,5,6-hexahydro-4-oxa(or thia)-10b-azafluoranthene nucleus which is substituted at position 3 or 3a with an alkanamine group. In addition, these compounds are useful antidepressant agents.

SUMMARY OF THE INVENTION

The compounds of this invention are represented by formula I

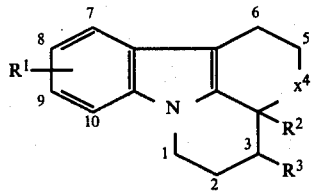

(I)

in which $R^1$ is hydrogen, lower alkyl, halo, nitro, trifluoromethyl or lower alkoxy; $R^2$ is a radical of formula Alk—$NR^4R^5$ wherein Alk is a straight or branched chain lower alkylene having one to six carbon atoms and $R^4$ and $R^5$ each is hydrogen or lower alkyl and $R^3$ is hydrogen, or $R^2$ is lower alkyl and $R^3$ is a radical of formula Alk—$NR^4R^5$ wherein Alk, $R^4$ and $R^5$ are as defined herein; and X is oxa or thia; or a therapeutically acceptable acid addition salt thereof.

The preferred compounds of this invention are represented by formula I in which $R^1$ is hydrogen; $R^2$ is a radical of formula Alk—$NR^4R^5$ wherein Alk is $(CH_2)_2$ or $(CH_2)_3$, and $R^4$ and $R^5$ each is hydrogen or lower alkyl, and $R^3$ is hydrogen, or $R^2$ is lower alkyl and $R^3$ is a radical of formula Alk—$NR^4R^5$ wherein Alk is $CH_2$, $R^4$ and $R^5$ are as defined herein; and X is oxa; or a therapeutically acceptable acid addition salt thereof.

A still more preferred group of compounds are represent by formula I in which $R^1$ is hydrogen; $R^2$ is a radical of formula Alk—$NR^4R^5$ wherein Alk is $(CH_2)_2$, $R^4$ is hydrogen or lower alkyl and $R^5$ is lower alkyl; $R^3$ is hydrogen; and X is oxa; or a therapeutically acceptable acid addition salt thereof.

The compounds of formula I in which $R^1$, $R^2$, $R^3$ and X are as defined herein are prepared by a process which comprises:

cyclizing an alcohol of formula V

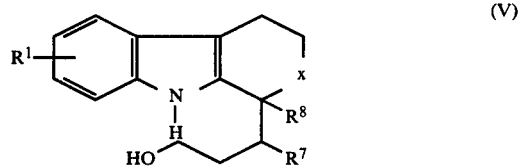

(V)

in which $R^1$ and X are as defined herein; $R^7$ is hydrogen and $R^8$ is a radical of formula CO—$NR^4R^5$ wherein $R^4$ and $R^5$ are as defined herein or Alk—CO—$NR^4R^5$ wherein Alk, $R^4$ and $R^5$ are as defined herein, or $R^7$ is a radical of formula CO—$NR^4R^5$ wherein $R^4$ and $R^5$ are as defined herein or Alk—CO—$NR^4R^5$ wherein Alk, $R^4$ and $R^5$ are as defined herein and $R^8$ is lower alkyl; to obtain the corresponding compound of formula VIII

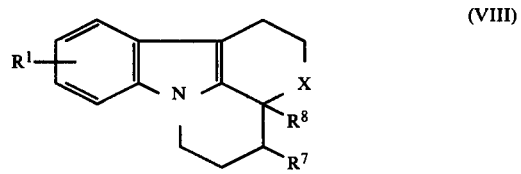

(VIII)

in which $R^1$, $R^7$, $R^8$ and X are as defined herein;

reducing the compound of formula VIII in which $R^1$ and X are as defined herein; $R^7$ is hydrogen and $R^8$ is a radical of formula CO—$NR^4R^5$ wherein $R^4$ and $R^5$ are as defined herein or Alk—CO—$NR^4R^5$ wherein Alk is $Alk^1$ in which $Alk^1$ is a straight or branched chain lower alkylene having one to five carbon atoms and $R^4$ and $R^5$ are as defined herein, or $R^7$ is a radical of formula CO—$NR^4R^5$ wherein $R^4$ and $R^5$ are as defined herein or Alk—$CONR^4R^5$ wherein Alk is $Alk^1$ in which $Alk^1$ is as defined herein and $R^4$ and $R^5$ are as defined herein and $R^8$ is lower alkyl; with a complex metal hydride to obtain the corresponding compound of formula I in which $R^1$ and X are as defined herein; $R^2$ is a radical of formula Alk—$NR^4R^5$ wherein Alk is $CH_2$ or $Alk^1$—$CH_2$ in which $Alk^1$ is as defined herein and $R^4$ and $R^5$ are as defined herein and $R^3$ is hydrogen, or $R^2$ is lower alkyl and $R^3$ is a radical of formula Alk—$NR^4R^5$ wherein Alk is $CH_2$ or $Alk^1$—$CH_2$ in which $Alk^1$ is as defined herein and $R^4$ and $R^5$ are as defined herein; or hydrolyzing the compound of formula VIII in which $R^1$ and X are as defined herein; $R^7$ is hydrogen and $R^8$ is a radical of formula Alk—CO—$NR^4R^5$ wherein Alk, and $R^4$ and $R^5$ are as defined herein, or $R^7$ is a radical of formula Alk—CO—$NR^4R^5$ wherein Alk, $R^4$ and $R^5$ are as defined herein and $R^8$ is lower alkyl; to obtain the corresponding acid; subjecting the latter acid to Curtius rearrangement to obtain the corresponding compound of formula I in which $R^1$ and X are as defined herein; $R^2$ is a radical of formula Alk—$NR^4R^5$ wherein Alk is as defined herein and $R^4$ and $R^5$ are hydrogen and $R^3$ is hydrogen, or $R^2$ is lower alkyl and $R^3$ is a radical of formula Alk—$NR^4R^5$ wherein Alk is as defined herein and $R^4$ and $R^5$ are hydrogen; and when desired, alkylating the latter compound of formula I to obtain the corresponding compound of formula I in which $R^1$ and X are as defined herein; $R^2$ is a radical of formula Alk—$NR^4R^5$ wherein Alk is as defined herein, $R^4$ is lower alkyl and $R^5$ is hydrogen or lower lower alkyl and $R^3$ is hydrogen, or $R^2$ is lower alkyl and $R^3$ is a radical of formula Alk—$NR^4R^5$ wherein Alk is as defined herein, $R^4$ is lower alkyl and $R^5$ is hydrogen or lower alkyl.

A compound of this invention is useful for treating depression in a mammal. Accordingly, an effective amount of a compound of formula I, or a therapeutically acceptable acid addition salt is administered to said mammal. A compound of formula I, or a therapeutically acceptable acid addition salt thereof, and a pharmaceutically acceptable carrier forms useful pharmaceutical composition for treating depression in the above manner.

DETAILED DESCRIPTION OF THE INVENTION

The term "lower alkyl" as used herein means straight chain alkyl radicals containing from one to six carbon atoms and branched chain alkyl radicals containing three or four carbon atoms and includes methyl, ethyl, propyl, isopropyl, butyl, isobutyl, pentyl, hexyl and the like.

The term "lower alkoxy" as used herein means straight chain alkoxy radicals containing from one to six carbon atoms and branched chain alkoxy radicals containing three or four carbon atoms and includes methoxy, ethoxy, isopropoxy, butoxy, hexanoxy and the like.

The term "lower alkylene" as used herein means a divalent organic radical derived from either straight or branched chain aliphatic hydrocarbons containing from one to six carbon atoms by removal of two hydrogen atoms and includes methylene, ethylene, 1-methylpropylene, 2-ethylpropylene, 2-butylethylene and the like.

The term "lower alkanoyl" as used herein means straight chain alkanoyl radicals containing from two to seven carbon atoms and a branched chain alkanoyl radical containing four or five carbon atoms and includes acetyl, propionyl, isobutyryl, hexanoyl and the like.

The term "lower alkanol" as used herein means both straight and branched chain alkanols containing from one to four carbon atoms and includes methanol, ethanol, isopropanol, butanol and the like.

The term "strong inorganic proton acceptor" as used herein means the inorganic bases, preferably the alkali metal hydrides, amides and alkoxides, for example, sodium ethoxide, sodamide, sodium methoxide, sodium hydride and the like.

The term "halo" as used herein means halogens and includes fluorine, chlorine, bromine and iodine, unless stated otherwise.

The term "organic proton acceptor" as used herein means the organic bases, or amines for instance, triethylamine, pyridine, N-ethylmorpholine, 1,5-diazabicyclo[3.4.0]-nonene-5 and the like.

The term "complex metal hydride" as used herein means the metal hydrides, including lithium aluminum hydride, lithium aluminum hydride-aluminum chloride, aluminum hydride-aluminum chloride, diborane, borane-methyl sulfide, sodium borohydride-aluminum chloride, diisobutylaluminum hydride and the like.

The term "complex borohydride" as used herein means the metal borohydrides, including sodium borohydride, potassium borohydride, lithium borohydride, zinc borohydride and the like, and metal trihydrocarbyl-borohydrides including lithium 9-alkyl-9-borabicyclo[3,3,1]-nonylhydride, in which the alkyl contains one to seven carbon atoms, preferably lithium 9-tert-butyl-9-borabicyclo[3,3,1]-nonylhydride, prepared according to the procedure described in German Offenlegungsschrift 2,207,987, published August 31, 1972, lithium diisopinocamphenyl-tert-butylborohydride and lithium 2-thexyl-4,8-dimethyl-2-borobicyclo[3,3,1]-nonylhydride, described by E. J. Corey et al., J. Amer. Chem. Soc., 93, 1491 (1971), lithium perhydro-9b-borophenalylhydride, described by H. C. Brown and W. C. Dickason, J. Amer. Chem. Soc., 92, 709 (1970) and the like.

The compounds of this invention are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture. These salts, when administered to a mammal, possess the same pharmacologic activities as the corresponding bases. For many purposes it is preferable to administered the salts rather than the base compounds. Examples of suitable acids to form these salts include: the common mineral acids, e.g., hydrohalic, sulfuric or phosphoric acids; the organic acids, e.g., formic, acetic, maleic, malic, citric, or tartaric acid; and acids which are sparingly soluble in body fluids and which impart slow-release properties to their respective salts, e.g., pamoic acid tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

Also included in this invention are the stereochemical isomers of the compounds of formula I which result from asymmetric centers contained therein. It is to be understood that the diastereomers arising from such asymmetry are included within the scope of this invention. Such diastereomers are obtained in substantially pure form by classical separation techniques and by sterically controlled synthesis and have arbitrarily been named as isomers A and B, respectively.

Individual optical enantiomers, which might be separated by fractional crystalization of the diastereomeric salts thereof, for instance, salts with d- or l-tartaric acid or D-(+)-α-bromocamphor sulfonic acid, are also included.

The antidepressant activity of the compounds of formula I, or their acid addition salts with therapeutically acceptable acids, is demonstrated in standard pharmacologic tests such as, for example, the tests described by F. Hafliger and V. Burckhart in "Psychopharmacological Agents," M. Gordon, Ed., Academic Press, New York and London, 1964, pp. 75–83.

More specifically, as noted in the latter reference, the antidepressant properties of a compound may be demonstrated by its capacity to prevent the depressant effects of reserpine. Furthermore, it is well documented that reserpine in animals produces a model depression which can be used for detecting antidepressant properties. Accordingly, the compounds of the present invention prevent reserpine effects in mice at doses ranging from about 1 to 200 mg per kilogram of body weight.

The following compounds of formula I are effective antidepressant agents when administered intraperitoneally to the mouse (the effective i.p. dose to achieve an $ED_{50}$ in mg per kilogram of body weight is indicated in the parentheses); 3a-[2-(dimethylamino)ethyl]-1,2,3,3a,5,6-hexahydro-4-oxa-10b-azafluoranthene (3.0–4.5 mg, described in Example II) and 1,2,3,3a,5,6-hexahydro-3a-[2-(methylamino)ethyl]-4-oxa-10b-azafluoranthene (6–9 mg, described in Example 12).

When the compounds of formula I of this invention are used as antidepressant agents in mammals, e.g., rats and dogs, they are used alone or in combination with pharmacologically acceptable carriers, the proportion of which is determined by the solubility and chemical nature of the compound, chosen route of administration and standard biological practice. For example, they are administered orally in solid form, e.g., capsule or tablet. They can also be administered orally in the form of suspensions or solutions or they can be injected parenterally. For parenteral administration they are used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the invention contain the active ingredient in admixture with one or more non-toxic pharmaceutical excipients known to be suitable in the manufacture of aqueous suspensions. Suitable excipients are, for example, methyl-cellulose, sodium alginate, gum acacia, lecithin and so forth. The aqueous suspensions can also contain one or more preservatives, one or more coloring agents, one or more flavouring agents and one or more sweetening agents.

Non-aqueous suspensions can be formulated by suspending the active ingredient in a vegetable oil, for example, arachic oil, olive oil, sesame oil, or coconut oil, or in a mineral oil. The suspension can contain a thickening agent, for example beeswax, hard paraffin or cetyl alcohol. These compositions can also contain a sweetening agent, flavouring agent and antioxidant.

The dosage of the compounds of formula I of this invention as antidepressant agents will vary with the form of administration and the particular compound chosen. Furthermore, it will vary with the particular host, as well as the age and condition of the host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. The effective antidepressant amount of the compounds usually ranges from about 0.1 mg to about 500 mg per kilogram of body weight per day, although as aforementioned variations will occur. However, a dosage level that is in the range of from about 1.0 mg to about 100 mg per kilogram of body weight per day is employed most desirably in order to achieve effective results.

Process

For the preparation of the 10b-azafluoranthene derivatives of this invention we prefer to use as starting materials the indoles of formula II

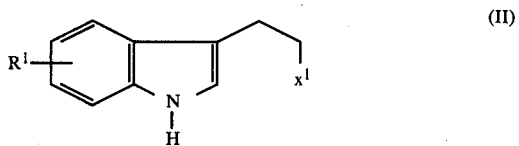

(II)

in which $R^1$ is as defined herein and $X^1$ is hydroxy or mercapto. The starting materials of formula II are either known or they may be obtained by methods described by C. A. Demerson et al. in U.S. Pat. No. 3,843,681, issued Oct. 22, 1974.

The first step in the process for preparing the compounds of formula I is the condensation of the compound of formula II with a ketone of formula III $$R^6-CH_2-CH(R^7)-CO-R^8 \qquad (III)$$

in which $R^6$ is $COOR^9$ wherein $R^9$ is lower alkyl, or $CH_2O-CO-R^{10}$ wherein $R^{10}$ is lower alkyl; $R^7$ is hydrogen and $R^8$ is a radical of formula $CO-NR^4R^5$ wherein $R^4$ and $R^5$ are as defined herein, Alk—CO—$NR^4R^5$ wherein Alk, $R^4$ and $R^5$ are as defined herein, $CO-OR^{11}$ wherein $R^{11}$ is lower alkyl or Alk—CO—$OR^{11}$ wherein Alk and $R^{11}$ are as defined herein; or $R^7$ is a radical of formula $CO-NR^4R^5$ wherein $R^4$ and $R^5$ are as defined herein, Alk—CO—$NR^4R^5$ wherein Alk, $R^4$ and $R^5$ are as defined herein, $CO-OR^{11}$ wherein $R^{11}$ is as defined herein or Alk—CO—$OR^{11}$ wherein Alk and $R^{11}$ are as defined herein and $R^8$ is lower alkyl in the presence of a suitable acid catalyst to obtain the corresponding compound of formula IV

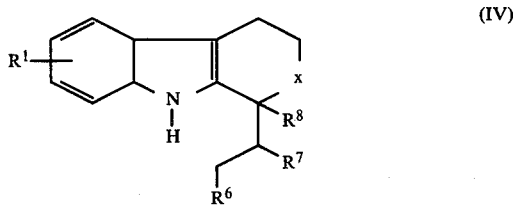

(IV)

in which $R^1$, $R^6$, $R^7$ and $R^8$ are as defined herein.

In practising the condensation (II+III→IV) we have found it preferable to use a solvent as a reaction medium. Any solvent inert to the reaction conditions may be used. Suitable solvents include benzene, toluene, diethyl ether, dioxan, tetrahydrofuran, methylene dichloride, carbon tetrachloride and the like. Benzene and tetrahydrofuran are especially convenient and practical for this use. A variety of suitable acid catalysts may be used for this condensation, for example, the type of catalyst used in a Fischer Indole Synthesis, i.e., p-toluenesulfonic acid, phosphorus pentoxide, boron trifluoride, zinc chloride, hydrochloric acid and sulfuric acid and the like. p-Toluenesulfonic acid, boron trifluoride and phosphorus pentoxide are included among the preferred acid catalysts. The amount of acid catalyst used is not especially critical and may range from 0.01 molar equivalents to 100 molar equivalents; however, a range of from 0.1 to 10 molar equivalents is generally preferred. The time of the reaction may range from 10 minutes to 60 hours, with the preferred range being from ½ to 24 hours. The temperature of the reaction may range from −20° C. to the boiling point of the reaction mixture. Preferred temperature ranges include 20° to 120° C.

The ketones of formula III are either known, for example, diethyl 4-oxopimelate, or they may be prepared by known methods described in general organic chemistry textbooks. For example, a comprehensive review on the properties and preparation of ketoesters and ketoamides may be found in "Rodd's Chemistry of Carbon Compounds," S. Coffey, Ed., Vol. 1d, 2nd ed., Elsevier Publishing Co., Amsterdam, 1965, pp. 49–54 and 226–274.

In the process for the preparation of the 10b-azafluoranthene ring system, the compounds of formula IV are converted to the corresponding alcohols of formula V (V)

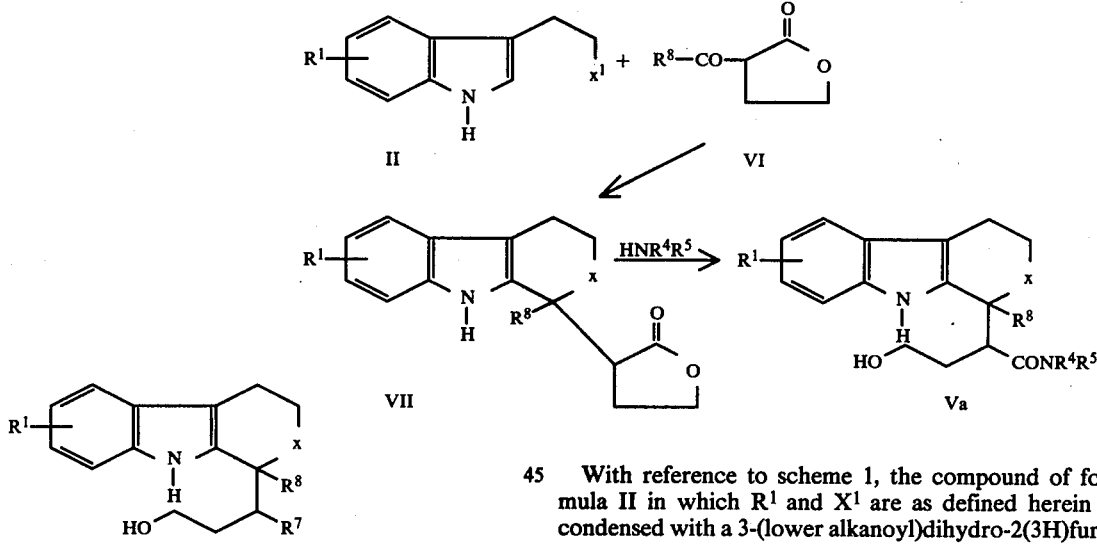

in which $R^1$ and X are as defined herein; $R^7$ is hydrogen and $R^8$ is a radical of formula CO—NR$^4$R$^5$ or Alk—CO—NR$^4$R$^5$, or $R^7$ is a radical of formula CO—NR$^4$R$^5$ or Alk—CO—NR$^4$R$^5$ and $R^8$ is lower alkyl.

The first step of this conversion requires that the compounds of formula IV in which $R^7$ or $R^8$ is a radical of formula CO—OR$^{11}$ or Alk—CO—OR$^{11}$ be converted to the corresponding amides of formula IV in which $R^7$ or $R^8$ is a radical of formula CO—NR$^4$R$^5$ or Alk—CO—NR$^4$R$^5$. A useful amidation method is the reaction of the ester of formula IV with about one molar equivalent of an amine of formula HNR$^4$R$^5$ wherein $R^4$ and $R^5$ are as defined herein in an inert solvent. Suitable inert solvents for this amidation can be selected from a lower alkanol, preferably methanol. The amidation usually requires a temperature ranging from 0° to 65° C. for one to ten days.

Subsequently, the compound of formula IV in which $R^7$ or $R^8$ is a radical of formula CO—NR$^4$R$^5$ or Alk—CO—NR$^4$R$^5$ and $R^6$ is COOR$^9$ or CH$_2$—O—CO—R$^{10}$ is reduced to obtain the corresponding alcohol of formula V. Suitable reducing agents are selected from complex borohydrides, preferably lithium borohydride. When the latter reducing agent is employed, the preferred solvents for the reduction include methanol, tetrahydrofuran and the like. Generally, the reduction with lithium borohydride is best performed at temperatures ranging from 20° to 65° C. for one to ten hours. While equivalent quantities of reactants may be used, it is preferably to use the reducing agent in moderate excess.

Alternatively, the compound of formula IV in which $R^7$ or $R^8$ is a radical of formula CO—NR$^4$R$^5$ or Alk—CO—NR$^4$R$^5$ and $R^6$ is CH$_2$O—CO—R$^{10}$ is hydrolyzed with an aqueous alcoholic solution of a suitable alkali, for example, sodium hydroxide in aqueous methanol, to afford the corresponding alcohol of formula V in which $R^1$, $R^7$ and $R^8$ are as defined herein.

In addition to the above described preparations of the alcohol of formula V other synthetic preparations are suitable for preparing specific alcohols of formula V. For instance, scheme 1 illustrates a preferred method of obtaining an alcohol of formula Va.

With reference to scheme 1, the compound of formula II in which $R^1$ and $X^1$ are as defined herein is condensed with a 3-(lower alkanoyl)dihydro-2(3H)furanone of formula VI in which $R^8$ is lower alkyl, in the same manner as described above for the condensation "II+III→IV," to obtain the corresponding compound of formula VII in which $R^1$ and X are as defined herein and $R^8$ is lower alkyl. The 3-(lower alkanoyl)-dihydro-2(3H)furanones of formula VI are known, for example, M. W. Wagle and T. B. Pause, Proc. Indian Acad. Sci. Sect. A, 68, 277 (1968). Subsequent reaction of the compound of formula VII with 10 to 40 molar equivalents of an amine of formula HNR$^4$R$^5$ in which $R^4$ and $R^5$ are as defined herein in an inert organic solvent, preferably tetrahydrofuran or dioxane, gives the corresponding alcohol of formula Va in which $R^1$, $R^4$, $R^5$ and X are as defined herein and $R^8$ is lower alkyl. This amidation usually requires a temperature of 45° to 100° C. for 10 to 30 hours. The alcohol of formula Va corresponds to the alcohol of formula V in which $R^1$ and X are as defined herein, $R^7$ is a radical of formula CO—NR$^4$R$^5$ wherein $R^4$ and $R^5$ are as defined herein and $R^8$ is lower alkyl.

It should be noted that the compounds of formula V in which $R^1$ and X are as defined herein, $R^7$ is CO—NR⁴R⁵ or Alk—CO—NR⁴R⁵ and R⁸ is lower alkyl, in addition to their use as intermediates for the preparation of the compounds of formula I, are useful also as intermediates for the preparation of the diuretic agents described in the copending U.S. Patent Application AHP-7121, filed as of same date.

Cyclization of the alcohol of formula V or Va gives the corresponding amido-10b-azafluoranthene of formula VIII

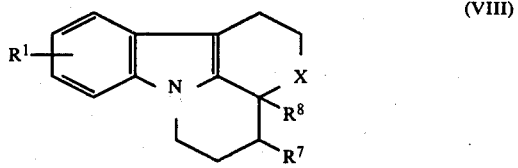

in which $R^1$ and X are as defined herein; $R^7$ is a radical of formula CO—NR⁴R⁵ or Alk—CO—NR⁴R⁵ and $R^8$ is lower alkyl, or $R^7$ is hydrogen and $R^8$ is a radical of formula CO—NR⁴R⁵ or Alk—CO—NR⁴R⁵.

The cyclization is conveniently effected by activating the alcohol followed by ring closure. A suitable and preferred method of activating the alcohol of formula V is to form the corresponding tosylate or mesylate. The mesylate is the preferred form of the activated alcohol. The mesylate is readily prepared by reacting the alcohol of formula V with two to four molar equivalents of methanesulfonyl chloride in the presence of two to four molar equivalents of an organic proton acceptor, preferably triethylamine, pyridine or N-ethylmorpholine, at $-15°$ to $5°$ C. for 5 to 60 minutes in an inert organic solvent, preferably methylene chloride or chloroform. Ring closure of the latter mesylate is achieved by reacting the mesylate with two to three molar equivalents of a strong inorganic proton acceptor, preferably sodium methoxide or sodium hydride. A suitable inert solvent for the cyclization can be selected from diethyl ether, tetrahydrofuran, toluene, dimethyl sulfoxide and dimethylformamide, preferably dimethylformamide. Usually the cyclization is complete after one to four hours at $10°$ to $40°$ C.

The amide group in the compound of formula VIII in which $R^7$ or $R^8$ is a radical of formula CO—NR⁴R⁵ or Alk—CO—NR⁴R⁵ wherein Alk is Alk¹ in which Alk¹ is a lower alkylene having one to five carbon atoms and $R^4$ and $R^5$ are as defined herein is reduced to obtain the corresponding compound of formula I. More specifically, the compound of formula VIII is reduced with three to five molar equivalents of a complex metal hydride to obtain the corresponding compound of formula I in which $R^1$ and X are as defined herein, $R^2$ is a radical of formula Alk—NR⁴R⁵ wherein Alk is $CH_2$ or Alk¹—$CH_2$ in which Alk¹ is as defined herein and $R^4$ and $R^5$ are as defined herein and $R^3$ is hydrogen; or $R^2$ is lower alkyl and $R^3$ is a radical of formula Alk—NR⁴R⁵ wherein Alk is $CH_2$ or Alk¹—$CH_2$ in which Alk¹ is as defined herein and $R^4$ and $R^5$ are as defined herein.

Examples of suitable complex metal hydrides are lithium aluminum hydride, lithium aluminum hydride-aluminum chloride, aluminum hydride-aluminum chloride, diborane, diisobutylaluminum hydride and sodium borohydride-aluminum chloride. Lithium aluminum hydride or diisobutylaluminum hydride is preferred. The preferred solvents for this reduction include the non-hydroxylic solvents, for example, diethyl ether, dioxane, tetrahydrofuran and 1,2-dimethoxyethane. Generally the reduction is best performed at temperatures ranging from $0°$ to $40°$ C., preferably $20°$ to $30°$ C., for 30 minutes to 24 hours. The latter compounds of formula I are isolated from the reaction mixture by conventional methods, for instance, see the Examples.

Other compounds of formula I also can be obtained from the amido-10b-azafluoranthene of formula VIII. For example, the amide group in the latter compound is hydrolysed under alkaline condition, preferably by heating a compound of formula VIII in which $R^7$ or $R^8$ is a radical of formula Alk—CO—NR⁴R⁵ wherein Alk, $R^4$ and $R^5$ are as defined herein in a solution of 10 to 20% sodium or potassium hydroxide at $80°$ to $100°$ C. for 10 to 30 hours, and then acidifying to obtain the corresponding carboxylic acid. This acid is then subjected to the Curtius rearrangement reactions, see the review by J. H. Saunders and R. J. Slocombe, Chem. Rev., 43, 205 (1948) for the general conditions for this reaction.

A preferred method of obtaining the Curtius rearrangement involves the following steps: The latter carboxylic acid is activated, preferably by reacting the carboxylic acid with 1.3 to 2.0 molar equivalents of ethyl chloroformate in the presence of an organic proton acceptor, i.e., triethylamine, in tetrahydrofuran at $0°$ to $5°$ C. for 30 to 100 minutes, to obtain a solution containing the corresponding activated carboxylic acid as the mixed anhydride. A solution of sodium azide (1.3 to 2.0 molar equivalents) in water is slowly added to the solution of the mixed anhydride at $-15°$ to $-5°$ C. and the combined solution is stirred at the latter temperature for 30 to 100 minutes to obtain the corresponding azide. A solution of the latter azide in benzene or toluene is heated at $50°$ to $100°$ C. for 15 to 60 minutes to obtain the corresponding isocyanate. In the next step, a solution of the isocyanate in 80 to 100% formic acid is stirred at $20°$ to $30°$ C. for one to five hours and separation of the reaction mixture affords the corresponding compound of formula I in which $R^2$ or $R^3$ is a radical of formula Alk—NR⁴R⁵ wherein Alk is as defined herein and $R^4$ and $R^5$ are hydrogen as well as the corresponding N-formyl derivative of the latter compound.

The latter formamide is reacted with two to four molar equivalents of a strong inorganic base, preferably sodium hydride, in an inert organic solvent, preferably xylene, at $100°$ to $140°$ C. for 10 to 30 hours and the solution is cooled to $20°$ to $30°$ C. An excess, preferably two to ten molar equivalents, of a lower alkyl iodide, chloride or bromide is added to the latter solution and the resulting solution is heated at $100°$ and $140°$ C. for one to five hours to obtain the corresponding N-(lower alkyl)formamide.

Reduction of the latter compound with a complex metal hydride, preferably lithium aluminum hydride, in the same manner as described above, gives the corresponding compound of formula I in which $R^2$ or $R^3$ is a radical of formula Alk—NR⁴R⁵ wherein Alk is as defined herein, $R^4$ is methyl and $R^5$ is lower alkyl.

Alternatively, the above described N-(lower alkyl)-formamide is hydrolyzed with an aqueous alkaline solution, preferably 10% sodium or potassium hydroxide at 80 to 100% for two to ten hours, to obtain the corresponding compound of formula I in which $R^2$ or $R^3$ is a radical of formula Alk—NR⁴R⁵ wherein Alk is as defined herein, $R^4$ is hydrogen and $R^5$ is lower alkyl.

If desired, the latter compound of formula I can be alkylated with a lower alkyl iodide, chloride or bromide, in the same manner as described above, to obtain the corresponding compound of formula I in which $R^2$ or $R^3$ is a radical of formula Alk—$NR^4R^5$ wherein Alk is as defined herein and $R^4$ and $R^5$ each is lower alkyl.

The following examples illustrate further this invention.

EXAMPLE 1

Dihydro-3-(1,3,4,9-tetrahydro-1-methylpyrano[3,4-b]indol-1-yl)-2(3H)-furanone (VII; $R^1$=H, $R^8$=$CH_3$ and X=O)

To a solution consisting of 3-acetyldihydro-2(3H)-furanone (25.6 g, 0.2 mole), tryptophol (32.2 g, 0.2 mole) and benzene (700 ml), p-toluenesulfonic acid (0.50 g) is added. The flask is equipped with a water separator and a condenser. The mixture is stirred at reflux for one hr. More p-toluenesulfonic acid (0.50 g) is added and the solution is refluxed for 18 hr. The dark solution is cooled and stirred in presence of silica gel (100 g) for 5 min. The mixture is filtered on diatomaceous earth and charcoal. The silica gel is washed with diethyl ether (2×100 ml) and the filtrates are evaporated to afford an oil which is a mixture of two diasteroisomers of the title compound. If desired, the latter oil can be crystallized from methanol to obtain crystals (17 g) of isomer A of the title compound, mp 162°–164° C. The mother liquor of this crystallization is evaporated to obtain a residue (20 g) containing mainly isomer B of the title compound.

EXAMPLE 2

1,3,4,9-Tetrahydro-α-(2-hydroxyethyl)-N,N,1-trimethylpyrano[3,4-b]indole-1-acetamide (V; $R^1$=H, $R^7$=$CON(CH_3)_2$, $R^8$=$CH_3$ and X=O)

A solution of the oil containing the two diasteriomers of dihydro-3-(1,3,4,9-tetrahydro-1-methylpyrano[3,4-b]indol-1-yl)-2(3H)furanone (described in Example 1, 15 g, 0.055 mole) in tetrahydrofuran (200 ml) and an aqueous solution of dimethylamine (40%, 200 ml) is refluxed for 24 hr. Aqueous sodium chloride solution is added and the solution is extracted with diethyl ether. The organic extract is dried and evaporated to afford an oil consisting of two diasteriomeric amides of the title compound. The oil is subjected to chromatography on silica gel using acetone-benzene (1:3). The eluates are evaporated and crystallized from benzene-hexane to obtain isomer A of the title compound as crystals (4.5 g), mp 158°–160° C. Further elution of the column with acetone-benzene (1:1), evaporation of the eluates and crystallization of the residue from benzene-hexane gives isomer B of the title compound as crystals (1.5 g), mp 159°–162° C.

In the same manner but replacing dimethyl amine with an equivalent amount of ammonia, methylethylamine, propylamine or di(2-methylpropyl)amine, the following compounds of formula V are obtained respectively, 1,3,4,9-tetrahydro-α-(2-hydroxyethyl)-1-methylpyrano[3,4-b]indole-1-acetamide, 1,3,4,9-tetrahydro-α-(2-hydroxyethyl)-N-ethyl-N,1-dimethylpyrano[3,4-b]indole-1-acetamide, 1,3,4,9-tetrahydro-α-(2-hydroxyethyl)-N-propyl-1-methylpyrano[3,4-b]indole-1-acetamide and 1,3,4,9-tetrahydro-α-2(2-hydroxyethyl)-N,N-di(2-methylpropyl)-1-methylpyrano[3,4-b]indole-1-acetamide.

EXAMPLE 3

1,2,3,3a,5,6-Hexahydro-N,N,3a-trimethyl4-oxa-10b-azafluoranthene-3-carboxamide (VIII; $R^1$=H, $R^7$=$CON(CH_3)_2$, $R^8$=$CH_3$ and X=O)

To a solution of 1,3,4,9-tetrahydro-α-(2-hydroxyethyl)-N,N,1-trimethylpyrano[3,4-b]indole-1-acetamide (isomer A, described in Example 2) 15 g, 0.047 mole) in methylene chloride (250 ml) is added triethylamine (15 ml, 0.11 mole) followed by a dropwise addition of methanesulfonyl chloride (8.4 ml, 0.11 mole) at 0° to −10° C. The reaction is stirred at 0° to −10° C. for 10 to 15 min. The reaction mixture is transferred to a separatory funnel and washed with ice-water and saturated sodium chloride solution. The organic solution is dried and evaporated to give the mesylate. The mesylate is dissolved in dimethylformamide (70 ml) and the solution is slowly added with stirring under nitrogen to a suspension of sodium hydride (4.5 g, 50% dispersion) in dimethylformamide (30 ml) while maintaining the temperature under 40° C. The reaction mixture is stirred for two hr. The solution is cooled to 0° C. and water is added cautiously to destroy excess sodium hydride. After dilution with more water, the solution is extracted with diethyl ether. The organic phase is washed with saturated sodium chloride solution, dried and evaporated. The residue is subjected to chromatography on silica gel using acetone-benzene (15:85). The eluate is evaporated and crystallized from a mixture of benzene, diethyl ether and hexane to give isomer A of the title compound (6.5 g), mp 166°–168° C.

In the same manner but replacing isomer A of the starting material with the corresponding isomer B, described in Example 2, isomer B of the title compound, mp 126°–128° C., is obtained.

In the same manner but replacing 1,3,4,9-tetrahydro-α-(2-hydroxyethyl)N,N,1-trimethylpyrano[3,4-b]indole-1-acetamide with an equivalent amount of another compound of formula V, described in Example 2, the following compounds of formula VIII are obtained respectively, 1,2,3,3a,5,6-hexahydro-3a-methyl-4-oxa-10b-azafluoranthene-3-carboxamide, 1,2,3,3a,5,6-hexahydro-N-ethyl-N,3a-dimethyl-4-oxo-10b-azafluoranthene-3-carboxamide, 1,2,3,3a,5,6-hexahydro-N-propyl-3a-methyl-4-oxa-10b-azafluoranthene-3-carboxamide and 1,2,3,3a,5,6-hexahydro-N,N-di(2-methylpropyl)-3a-methyl-4-oxa-10b-azafluoranthene-3-carboxamide.

EXAMPLE 4

3-[(Dimethylamino)methyl]-1,2,3,3a,5,6-hexahydro-3a-methyl-4-oxa-10b-azafluoranthene (I; $R^1$=H, $R^2$=$CH_3$, $R^3$=$CH_2N(CH_3)_2$ and X=O)

A solution of 1,2,3,3a,5,6-hexahydro-N,N,3a-trimethyl-4-oxa-10b-azafluoranthene-3-carboxamide isomer A (described in Example 3, 10 g, 0.035 mole) in dry tetrahydrofuran (100 ml) is added dropwise under nitrogen to a stirred solution of diisobutylaluminum hydride (20 g, 0.14 mole) in hexane (60 ml) at −20° C. The mixture is stirred for 30 min. at −20° to −10° C. The organometallic complex is decomposed by dropwise addition with cooling of a mixture of petroleum ether and methanol. Dilute sulfuric acid (10%, 100 ml) is added. The solution is washed with diethyl ether, basified and extracted with diethyl ether. The latter ether layer is washed with a saturated sodium chloride solution, dried over magnesium sulfate, filtered through charcoal and diatomaceous earth, and evaporated to give isomer A of the title compound, (9.0 g), nmr (CDCl$_3$) δ 1.49, 2.34, 4.16 and 7.21. To a solution of the latter compound in diethyl ether (300 ml), maleic acid (3.7 g, 0.032 mole) in acetone (20 ml) is added dropwise. The maleate salt which crystallizes out of the solution is filtered and recrystallized from a solvent composed of dichloromethane (200 ml), benzene (100 ml) and diethyl ether (200 ml) to give the maleate salt (10.5 g), mp 140°–142° C., of isomer A of the title compound.

In the same manner but replacing isomer A of the starting material with the corresponding isomer B (described in Example 3), isomer B of the title compound, mp 134°–137° C. (crystallized from diethyl ether), and the maleate salt, mp 157°–160° C. (crystallized from dichloromethane-benzene-diethyl ether), of isomer B of the title compound, are obtained.

Similarily, replacing 1,2,3,3a,5,6-hexahydro-N,N,3a-trimethyl-4-oxa-10b-azafluoranthene-3-carboxamide with an equivalent amount of another compound of formula VIII, described in Example 3, the following compounds of formula II are obtained respectively, 3-aminomethyl-1,2,3,3a,5,6-hexahydro-3a-methyl-4-oxa-10b-azafluoranthene, 3-[(N-ethyl-N-methylamino)methyl]-1,2,3,3a,5,6-hexahydro-3a-methyl-4-oxa-10b-azafluoranthene, 3-[(propylamino)methyl]-1,2,3,3a,5,6-hexahydro-3a-methyl-4-oxa-10b-azafluoranthene and 3-[[di(2-methylpropyl)amino]methyl]-1,2,3,3a,5,6-hexahydro-3a-methyl-4-oxa-10b-azafluoranthene.

By replacing tryptophol in Example 1 with an equivalent amount of indole-3-ethanethiol, 4-ethyl-indole-3-ethanol, 7-bromo-indole-3-ethanol, 6-nitro-indole-3-ethanethiol, 5-trifluoromethyl-indole-3-ethanol or 5-propoxy-indole-3-ethanol and following the procedures of Examples 1 to 4, the following compounds of formula I are obtained respectively: 3-[(dimethylamino)methyl]-1,2,3,3a,5,6-hexahydro-3a-methyl-4-thia-10b-azafluoranthene, 3-[(dimethylamino)methyl]-7-ethyl-1,2,3,3a,5,6-hexahydro-3a-methyl-4-oxa-10b-azafluoranthene, 10-bromo-3-[(dimethylamino)methyl]-1,2,3,3a,5,6-hexahydro-3a-methyl-4-oxa-10b-azafluoranthene, 3-[(dimethylamino)methyl]-1,2,3,3a,5,6-hexahydro-3a-methyl-9-nitro-4-thia-10b-azafluoranthene, 3-[(dimethylamino)methyl]1,2,3,3a,5,6-hexahydro-3a-methyl-4-oxa-8-trifluoromethyl-10b-azafluoranthene and 3-[(dimethylamino)methyl]-1,2,3,3a,5,6-hexahydro-3a-methyl-4-oxa-8-propoxy-10b-azafluoranthene.

Similarly, replacing 3-acetyldihydro-2(3H)-furanone in Example 1 with an equivalent amount of 3-propionyldihydro-2(3H)furanone, 3-pentionyldihydro-2(3H)furanone or 3-(4-methylpentionyl)dihydro-2(3H) furanone and following the procedures of Examples 1 to 4, the following compounds of formula I are obtained respectively: 3-[(dimethylamino)methyl]-1,2,3,3a,5,6-hexahydro-3a-ethyl-4-oxa-10b-azafluoranthene, 3-[(dimethylamino)methyl]-1,2,3,3a,5,6-hexahydro-3a-butyl-4-oxa-10b-azafluoranthene and 3-[(dimethylamino)methyl]-1,2,3,3a,5,6-hexahydro-3a-(3-methylbutyl)-4-oxa-10b-azafluoranthene.

EXAMPLE 5

1,3,4,9-Tetrahydropyrano[3,4-b]indole-1,1-dipropionic Acid Diethyl Ester (IV; $R^1$=H, $R^6$=COOEt, $R^7$=H, $R^8$=CH$_2$CH$_2$COOEt and X=O)

To a solution consisting of tryptophol (48.3 mole), diethyl 4-oxopimelate (70.6 g, 0.31 mole) and benzene (1000 ml), p-toluenesulfonic acid (9.6 g) is added. The flask is equipped with a water separated and a condenser. The mixture is stirred at reflux for 4 hr. The dark solution is cooled, stirred in presence of silica gel (125 g) and charcoal, filtered through diatomaceous earth and the filtrate is concentrated. The residue is subjected to chromatography on silica-gel using 20% ethyl acetate in benzene as eluant. The eluates are allowed to stand at room temperature for one month and crystals are obtained. The crystals are collected and analyzed to be crystals (9.2 g) of 1,2,3,3a,5,6-hexahydro-1-oxo-4-oxa-azafluoranthene-3a-propionic acid ethyl ester, mp 90°–93° C. The mother liquor is evaporated to give a residue of the title compound, nmr (CDCl$_3$) δ 1.04–1.35(m), 2.15–3.00(m), 3.85–4.35(m), 7.0–7.6(m) and 8.3(s).

In the same manner but replacing diethyl 4-oxopimelate with an equivalent amount of methyl 7-dipropylamino-4,7-dioxo-heptanoate, propyl 9-amino-4,9-dioxo-7-methyl-nonanoate or ethyl 8-(N-methyl-N-butylamino)-4,8-dioxo-octanoate, the following compounds of formula IV are obtained respectively: 1-[2-(dipropylcarbamoyl)ethyl]-1,3,4,9-tetrahydropyrano[3,4-b]indole-1-propionic acid methyl ester, 1-[(4-carbamoyl-3-methyl)butyl]-1,3,4,9-tetrahydropyrano[3,4-b]indole-1-propionic acid propyl ester and 1-[3-(N-methyl-N-butylcarbamoyl)propyl]-1,3,4,9-tetrahydropyrano[3,4-b]indole-1-propionic acid ethyl ester.

EXAMPLE 6

1-[2-(Dimethylcarbamoyl)ethyl]-1,3,4,9-tetrahydropyrano[3,4-b]indole-1-propionic Acid Methyl Ester (IV; $R^1$=H, $R^6$=COOEt, $R^7$=H, $R^8$=CH$_2$CH$_2$CON(CH$_3$)$_2$ and X=O)

A solution of 1,3,4,9-tetrahydropyrano[(3,4-b]indole-1,1-dipropionic acid diethyl ester (described in Example 5, 44 g) in methanol (150 ml) and dimethylamine (150 ml) is stirred under nitrogen at reflux for two days and at room temperature for four days. The solvent is evaporated and the residue is chromatographed on silica gel using acetone. The eluates are evaporated and the residue is crystallized from a solution of dichloromethane, diethyl ether and hexane to obtain crystals of the title compound (14.5 g), mp 137°–139° C.

In the same manner but replacing dimethylamine with an equivalent amount of ethylamine, butylamine or N-methyl-N-butylamine, the following compounds of formula (IV are obtained respectively: 1-[2-(ethylcarbamoyl)ethyl]-1,3,4,9-tetrahydropyrano[3,4-b]indole-1-propionic acid methyl ester, 1-[2-(butylcarbamoyl)ethyl]-1,3,4,9-tetrahydropyrano-[3,4-b]indole-1-propionic acid methyl ester and 1-[2-(N-methyl-N-butylcarbamoyl)ethyl]-1,3,4,9-tetrahydropyrano[3,4-b]indole-1-propionic acid methyl ester.

EXAMPLE 7

1,3,4,9-Tetrahydro-1-(3-hydroxypropyl)-N,N-dimethylpyrano[3,4-b]indole-1-propionamide (V; $R^1$ and $R^7$=H, $R^8$=CH$_2$CH$_2$CON(CH$_3$)$_2$ and X=O)

A solution 1-[2-(dimethylcarbamoyl)ethyl]-1,3,4,9-tetrahydropyrano[3,4-b]indole-1-propionic acid methyl ester (described in Example 6, 32 g, 0.09 mole) in dry tetrahydrofuran (250 ml) is added dropwise to a mechanically stirred solution of lithium borohydride (2.0 g, 0.09 mole) in dry tetrahydrofuran (200 ml) under nitrogen at room temperature. The mixture is stirred for three hr at reflux. After cooling in ice-water bath, 1 N hydrochloric acid (150 ml) is added dropwise. The aqueous solution is extracted with diethyl ether and the organic phase is washed with a saturated sodium chloride solution, dried over magnesium sulfate and evaporated. The residue (29 g) is crystallized from ethyl acetate-hexane to obtain crystals of the title compound, mp 64°–65° C.

In the same manner but replacing 1-[2-dimethylcarbamoyl)ethyl]-1,3,4,9-tetrahydropyrano[3,4-b]indole-1-propionic acid methyl ester with an equivalent amount of another compound of formula IV described in Examples 5 and 6, the following compounds of formula V are obtained respectively: 1,3,4,9-tetrahydro-1-(3-hydroxypropyl)-N,N-dipropyl-pyrano[3,4-b]indole-1-propionamide, 1,3,4,9-tetrahydro-1-(3-hydroxypropyl)-pyrano[3,4-b]indole-1-(3-methyl)pentionamide, 1,3,4,9-tetrahydro-1-(3-hydroxypropyl)-N-methyl-N-butyl-pyrano[3,4-b]indole-1-butionamide, 1,3,4,9-tetrahydro-1-(3-hydroxypropyl)-N-ethyl-pyrano[3,4-b]indole-1-propionamide, 1,3,4,9-tetrahydro-1-(3-hydroxypropyl)-N-butyl-pyrano[3,4-b]indole-1-propionamide and 1,3,4,9-tetrahydro-1-(3-hydroxypropyl)-N-methyl-N-butyl-pyrano[3,4-b]indole-1-propionamide.

EXAMPLE 8

1,2,3,3a,5,6-Hexahydro-N,N-dimethyl-4-oxa-10b-azafluoranthene-3a-propionamide (VIII; $R^1$ and $R^7$=H, $R^8$=CH$_2$CH$_2$CON(CH$_3$)$_2$ and X=O)

To a solution of 1,3,4,9-tetrahydro-1-(3-hydroxypropyl)-N,N-dimethylpyrano[3,4-b]indole-1-propionamide (described in Example 7, 39 g, 0.12 mole) in methylene chloride (500 ml) in added triethylamine (38 ml, 27.6 g, 0.274 mole), and methane-sulfonyl chloride (21 ml, 0.275 mole) dropwise at −10° to 0° C. under nitrogen and the solution is stirred for 10 to 15 min. The reaction mixture is transferred to a separatory funnel with the aid of more methylene chloride. The mixture is washed with a saturated sodium chloride solution, dried and evaporated to a residue of the mesylate. The mesylate is dissolved in dry dimethylformamide (200 ml) and slowly added with stirring under nitrogen to a suspension of sodium hydride (13.0 g, 50% dispersion, 0.27 mole) in dry dimethylformamide (100 ml). The temperature slowly goes to 50° C. and an exothermic reaction takes place. The temperature is kept below 65° C. with the aid of a dry ice-acetone bath. The mixture is stirred at room temperature for 18 hr after the addition is completed. The solution is cooled to 0° C. and water is added cautiously to destroy excess sodium hydride. After dilution with sodium chloride solution, the aqueous solution is extracted with diethyl ether. The organic phase is washed with saturated sodium chloride solution, dried and evaporated. The crystals which crystallizes upon concentration of solution are collected to obtain the title compound (16 g), mp 191°–103° C.

In the same manner but replacing 1,3,4,9-tetrahydro-1-(3-hydroxypropyl)-N,N-dimethyl-pyrano[3,4-b]indole-1-propionamide with an equivalent amount of another compound of formula V described in Example 7, the following compounds of formula VIII are obtained respectively: 1,2,3,3a,5,6-hexahydro-N,N-dipropyl-4-oxa-10b-azafluoranthene-3a-propionamide, 1,2,3,3a,5,6-hexahydro-4-oxa-10b-azafluoranthene-3a-(3-methyl)-pentionamide, 1,2,3,3a,5,6-hexahydro-N-methyl-N-butyl-4-oxa-10b-azafluoranthene-3a-butionamide, 1,2,3,3a,5,6-hexahydro-N-ethyl-4-oxa-10b-azafluoranthene-3a-propionamide, 1,2,3,3a,5,6-hexahydro-N-butyl-4-oxa-10b-azafluoranthene-3a-propionamide and 1,2,3,3a,5,6-hexahydro-N-methyl-N-butyl-4-oxa-10b-azafluoranthene-3a-propionamide.

EXAMPLE 9

3a-[3-(Dimethylamino)propyl]-1,2,3,3a,5,6-hexahydro-4-oxa-10b-azafluoranthene (I; $R^1$ and $R^3$=H, $R^2$=(CH$_2$)$_3$N(CH$_3$)$_2$ and X=O)

A solution of 1,2,3,3a,5,6-hexahydro-N,N-dimethyl-4-oxa-10b-azafluoranthene-3a-propionamide (described in Example 8, 2.0 g, 6.4 mmole) in anhydrous tetrahydrofuran (50 ml) is added dropwise to a mechanically stirred suspension of lithium aluminium hydride (0.50 g, 14.7 mmole) in anhydrous tetrahydrofuran (50 ml) under nitrogen and stirring is continued for two hr at room temperature. The excess hydride is destroyed by dropwise addition of water to the cooled mixture. Diethyl ether is added and the mixture is filtered through diatomaceous earth. The filtrate is washed once with brine, dried over magnesium sulfate and evaporated to give a residue of the title compound, nmr (CDl$_3$) δ 2.2 and 7.0–7.6. The maleate salt of the title compound is prepared in the same manner as described in Example 4 and crystallized from a mixture of dichloromethane, benzene and diethyl ether to obtain crystals (2.2 g), mp 145°–147° C.

In the same manner but replacing 1,2,3,3a,5,6-hexahydro-N,N-dimethyl-4-oxa-10b-azafluoranthene-3a-propionamide with an equivalent amount of another compound of formula VIII described in Example 8, the following compounds of formula I are obtain respectively: 3a-[3-(dipropylamino)propyl]-1,2,3,3a,5,6-hexahydro-4-oxa-10b-azafluoranthene, 3a-(5-amino-3-methyl-pentyl)-1,2,3,3a,5,6-hexahydro-4-oxa-10b-azafluoranthene, 3a-[4-(N-methyl-N-butylamino)butyl]-1,2,3,3a,5,6-hexahydro-4-oxa-10b-azafluoranthene, 3a-[3-(ethylamino)propyl]-1,2,3,3a,5,6-hexahydro-4-oxa-10b-azafluoranthene, 3a-[3-(butylamino)propyl]-1,2,3,3a,5,6-hexahydro-4-oxa-10b-azafluoranthene, 3a-[3-(N-methyl-N-butylamino)propyl]-1,2,3,3a,5,6-hexahydro-4-oxa-10b-azafluoranthene.

By replacing tryptophol in Example 5 with an equivalent amount of 5-methyl-indole-3-ethanethiol, 7-ethoxy-indole-3-ethanol, 4-chloro-indole-3-ethanol, 6-butyl-indole-ethanol, 5-nitro-indole-3-ethanethiol or 6-(1,1-dimethylethoxy)-indole-3-ethanol and following the procedures of Examples 5 to 9, the following compounds of formula I are obtained respectively: 3a-[3-(dimethylamino)propyl]-1,2,3,3a,5,6-hexahydro-8-methyl-4-thia-10b-azafluoranthene, 3a-[3-(dimethylamino)propyl]-1,2,3,3a,5,6-hexahydro-10-ethoxy-4-oxo-10b-azafluoranthene, 3a-[3-(dimethylamino)-propyl]-1,2,3,3a,5,6-hexahydro-7-chloro-4-oxa-10b-azafluoranthene, 3a-[3-(dimethylamino)-propyl]-1,2,3,3a,5,6-hexahydro-9-butyl-4-oxa-10b-azafluoranthene, 3a-[3-(dimethylamino)propyl]-1,2,3,3a,5,6-hexahydro-8-nitro-4-thia-10b-azafluoranthene and 3a-[3-(dimethylamino)propyl]-1,2,3,3a,5,6-hexahydro-9-(1,1-dimethylethoxy)-4-oxa-10b-azafluoranthene.

EXAMPLE 10

3a-(2-Aminoethyl)-1,2,3,3a,5,6-hexahydro-4-oxa-10b-azafluoranthene (I; $R^1$ and $R^3$=H, $R^2$=CH$_2$CH$_2$NH$_2$ and X=O)

A solution of 1,2,3,3a,5,6-hexahydro-N,N-dimethyl-4-oxa-10b-azafluoranthene-3a-propionamide (described in Example 8, 25 g, 0.08 mole) in a 10% potassium hydroxide solution (500 ml) is stirred at reflux for 18 hr.

The solution is cooled, washed with diethyl ether, acidified and extracted with diethyl ether. The organic phase is dried over sodium sulfate, evaporated and crystallized to give 1,2,3,3a,5,6-hexahydro-4-oxa-10b-azafluoranthene-3a-propionic acid (21.5 g), mp 153°–155° C.

To a mechanically stirred, ice cold solution of the latter compound (20.0 g, 0.070 mole) in dry tetrahydrofuran (300 ml) is added dropwise under an atmosphere of dry nitrogen, triethylamine (18 ml, 13 g, 0.13 mole) and ethyl chloroformate (10.5 ml, 11.7 g, 0.11 mole). After stirring for one hr at 0° C., the suspension is cooled to −10° C. and a solution of sodium azide (7.2 g, 0.11 mole) in distilled water (35 ml) is added dropwise. After stirring for one hr at −10° C., the reaction mixture is diluted with diethyl ether (200 ml) and decanted. The organic solution is dried over using magnesium sulfate, evaporated and crystallized from diethyl ether to obtain 1,2,3,3a,5,6-hexahydro-4-oxa-10b-azafluoranthene-3a-propionyl azide (21 g), mp 86°–87° C.

The latter compound (21.0 g) is dissolved in dry benzene (300 ml) and refluxed for 30 min and evaporated to obtain a residue of isocyanic acid 2-(1,2,3,3a,5,6-hexahydro-4-oxa-10b-azafluoranthene-3a-yl)ethyl ester (18 g), mp 89°–91° C.

To a stirring solution of the latter compound (18 g, 0.064 mole) in 250 ml of dry benzene at 10° C. is added dropwise 10 ml of 88% formic acid. After the addition of the formic acid is complete, the reaction mixture is allowed to reach room temperature and stirred for one hour. More 88% formic acid (1 ml) is added and the mixture is stirred for 30 min at 30°–40° C. The mixture is washed with cold sodium chloride solution, dried and evaporated. The residue is subjected to chromatography on silica gel using acetone-benzene (1:2) to obtain N-[2-(1,2,3,3a,5,6-hexahydro-4-oxa-10b-azafluoranthene-3a-yl)ethyl]formamide (7.0 g), nmr (CDCl$_3$) δ 2.18, 2.85, 3.45, 4.10, 6.25, 7.25 and 8.1. The above aqueous washing are basified with 10% sodium hydroxide and extracted with benzene. The organic extract is dried and evaporated to obtain a residue of the title compound (4.7 g), nmr (CDCl$_3$) δ 1.23, 2.18, 2.90, 3.60, 4.15 and 7.22. The maleate salt of the title compound is prepared in the same manner as described in Example 4 and crystallized from a mixture of methanol, benzene and diethyl ether to obtain crystals, mp 180°–181° C.

EXAMPLE 11

3a-[2-(Dimethylamino)ethyl]-1,2,3,3a,5,6-hexahydro-4-oxa-10b-azafluoranthene (I; R$^1$ and R$^3$=H, R$^2$=CH$_2$CH$_2$N(CH$_3$)$_2$ and X=O)

A mixture of sodium hydride (3.0 g, 50% oil dispension, 0.065 mole) and dry xylene (50 ml) is added into a dry three-neck round bottom flask, equipped with stirrer, reflux condenser and addition funnel. A solution of N-[2-(1,2,3,3a,5,6-hexahydro-4-oxa-10b-azafluoranten-3a-yl)ethyl]formamide (described in Example 10, 7.0 g, 0.025 mole) in xylene (100 ml) is added and the mixture is refluxed with stirring for 18 hr under an atmosphere of nitrogen. The reaction mixture is cooled to room temperature, the reflux condenser is replaced by an acetone-dry ice condenser; methyl iodide (15 ml) is added, and the reaction mixture is refluxed for two hr. After cooling, water is added to destroy excess sodium hydride and the organic layer is separated, washed with a saturated sodium chloride solution, dried and evaporated. The residue is subjected to chromatography on silica gel using acetone-benzene (1:2) and the eluates are evaporated. The residue is crystallized from diethyl ether to obtain crystals (6.0 g) of N-[2-(1,2,3,3a,5,6-hexahydro-4-oxa-10b-azafluoranthen-3a-yl)ethyl]-N-methylformamide, mp 111°–113° C.

A solution of the latter compound (3.0 g, 0.01 mole) in anhydrous tetrahydrofuran (100 ml) is added dropwise to a mechanically stirred suspension of lithium aluminium hydride (0.30 g, 0.009 mole) in anhydrous tetrahydrofuran (30 ml) under nitrogen. The mixture is stirred for two hr at 0° C. The excess hydride is destroyed by dropwise addition of water to the cooled mixture. Diethyl ether is added and the mixture is filtered through diatomaceous earth. The filtrate is extracted with 1 N hydrochloric acid (100 ml) and the aqueous phase is basified with a 10% sodium hydroxide solution. The alkaline aqueous solution is extracted with diethyl ether and the organic extract is evaporated to obtain a residue of the title compound (2.8 g), nmr (CDCl$_3$) δ 2.25 and 7.1–7.6. The maleate salt of the title compound is prepared in the same manner as described in Example 4 and crystallized from a mixture of methanol, benzene and diethyl ether to obtain crystals (2.3 g), mp 143°–145° C.

In the same manner but replacing methyl iodide with an equivalent amount of ethyl bromide, propyl chloride, hexyl iodide or 2-methylpropyl bromide, the following N-(lower alkyl) formamides are obtained respectively: N-[2-(1,2,3,3a,5,6-hexahydro-4-oxa-10b-azafluoranthen-3a-yl)ethyl]-N-ethylformamide, N-[2-(1,2,3,3a,5,6-hexahydro-4-oxa-10b-azafluoranthen-3a-yl)ethyl]-N-propylformamide, N-[2-(1,2,3,3a,5,6-hexahydro-4-oxa-10b-azafluoranthen-3a-yl)ethyl]-N-hexylformamide and N-[2-(1,2,3,3a,5,6-hexahydro-4-oxa-10b-azafluoranthene-3a-yl)ethyl]-N-(2-methylpropyl)formamide. In turn, the latter N-(lower alkyl)formamides are reduced with lithium aluminum hydride, in the same manner as described above above, and the following compounds of formula I are obtained respectively: 3a-[2-(N-ethyl-N-methylamino)ethyl]-1,2,3,3a,5,6-hexahydro-4-oxa-10b-azafluoranthene, 3a-[2-(N-methyl-N-propylamino)ethyl]-1,2,3,3a,5,6-hexahydro-4-oxa-10b-azafluoranthene, 3a-[2-(N-hexyl-N-methylamino)ethyl]-1,2,3,3a,5,6-hexahydro-4-oxa-10b-azafluoranthene and 3a-[2-[N-methyl-N-(2-methylpropyl)amino]ethyl]-1,2,3,3a,5,6-hexahydro-4-oxa-10b-azafluoranthene.

EXAMPLE 12

1,2,3,3a,5,6-Hexahydro-3a-[2-(methylamino)ethyl]-4-oxa-10b-azafluoranthene (I: R$^1$ and R$^3$=H, R$^2$=CH$_2$CH$_2$NHCH$_3$ and X=O)

A solution of N-[2-(1,2,3,3a,5,6-hexahydro-4-oxa-10b-azafluoranthen-3a-yl)ethyl]-N-methylformamide (described in Example 11, 1.0 g, 0.0033 mole) in 10% aqueous potassium hydroxide solution (25 ml) is refluxed for 5 hr. The solution is cooled and extracted with diethyl ether. The organic extract is dried and evaporated to give a residue of the title compound (0.7 g), nmr(CDCl$_3$) δ 1.6, 2.45 and 7.0–7.65. The maleate salt of the title compound is prepared in the same manner as described in Example 4 and crystallized from a mixture of methanol, dichloromethane and diethyl ether to obtain crystals (0.85 g), mp 151°–153° C.

In the same manner but replacing N-[2-(1,2,3,3a,5,6-hexahydro-4-oxa-10b-azafluoranthen-3a-yl)ethyl]-N-methylformamide with an equivalent amount of another N-(lower alkyl) formate, described in Example 11, the following compounds of formula I are obtained respectively: 1,2,3,3a,5,6-hexahydro-3a-[2-(ethylamino)ethyl]-

4-oxa-10b-azafluoranthene, 1,2,3,3a,5,6-hexahydro-3a-[2-(propylamino)ethyl]-4-oxa-10b-azafluoranthene, 1,2,3,3a,5,6-hexahydro-3a-[2-(hexylamino)ethyl]-4-oxa-10b-azafluoranthene and 1,2,3,3a,5,6-hexahydro-3a-[2-[(2-methylpropyl)amino]ethyl]-4-oxa-10b-azafluoranthene.

We claim:

1. A compound of formula 1

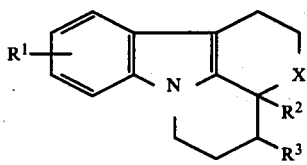

(I)

in which $R^1$ is hydrogen, lower alkyl, halo, nitro, trifluoromethyl or lower alkoxy; $R^2$ is a radical of formula Alk-NR$^4$R$^5$ wherein Alk is a straight or branched chain lower alkylene having one to six carbon atoms, and $R^4$ and $R^5$ each is hydrogen or lower alkyl and $R^3$ is hydrogen, or $R^2$ is lower alkyl and $R^3$ is a radical of formula Alk-NR$^4$R$^5$ wherein Alk, $R^4$ and $R^5$ are as defined herein; and X is oxa or thia; or a therapeutically acceptable acid addition salt thereof.

2. A compound of formula I

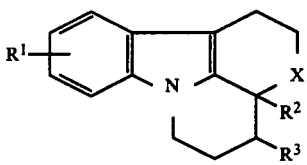

(I)

in which $R^1$ is hydrogen; $R^2$ is a radical of formula Alk-NR$^4$R$^5$ wherein Alk is $(CH_2)_2$ or $(CH_2)_3$, and $R^4$ and $R^5$ each is hydrogen or lower alkyl, and $R^3$ is hydrogen, or $R^2$ is lower alkyl and $R^3$ is a radical of formula Alk-NR$^4$R$^5$ wherein Alk is $CH_2$, and $R^4$ and $R^5$ are as defined herein; and X is oxa; or a therapeutically acceptable acid addition salt thereof.

3. A compound of formula I, as claimed in claim 2, wherein $R^1$ is hydrogen; $R^2$ is a radical of formula Alk-NR$^4$R$^5$ wherein Alk is $(CH_2)_2$, $R^4$ is hydrogen or lower alkyl and $R^5$ is lower alkyl; $R^3$ is hydrogen; and X is oxa; or a therapeutically acceptable acid addition salt thereof.

4. 3-[(Dimethylamino)methyl]-1,2,3,a,5,6-hexahydro-3a-methyl-4-oxa-10b-azafluoranthene, whose maleate salt has a melting point 140°–142° C., as claimed in claim 1.

5. 3-[(Dimethylamino)methyl]-1,2,3,a,5,6-hexahydro-3a-methyl-4-oxa-10b-azafluoranthene, whose maleate salt has a melting point 157°–160° C., as claimed in claim 1.

6. 3a-[3-(Dimethylamino)propyl]-1,2,3,3a,5,6-hexahydro-4-oxa-10b-azafluoranthene, as claimed in claim 1.

7. 3a-(2-Aminoethyl)-1,2,3,3a5,6-hexahydro-4-oxa-10b-azafluoranthene, as claimed in claim 1.

8. 3a-[2-(Dimethylamino)ethyl]-1,2,3,3a,5,6-hexahydro-4-oxa-10b-azafluoranthene, as claimed in claim 1.

9. 1,2,3,3a,5,6-Hexahydro-3a-[2-(methylamino)ethyl]-4-oxa-10b-azafluoranthene, as claimed in claim 1.

10. A compound of formula VIII

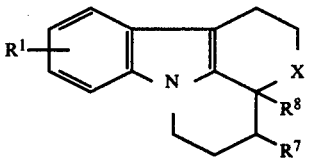

(VIII)

in which $R^1$ is hydrogen, lower alkyl, halo, nitro, trifluoromethyl or lower alkoxy; $R^7$ is hydrogen or a radical of formula CO-NR$^4$R$^5$ wherein $R^4$ and $R^5$ each is hydrogen or lower alkyl or Alk-CO-NR$^4$R$^5$ wherein Alk is a straight or branched chain lower alkylene having one to six carbon atoms and $R^4$ and $R^5$ are as defined herein; $R^8$ is lower alkyl or a radical of formula CO-NR$^4$R$^5$ wherein $R^4$ and $R^5$ are as defined herein or Alk-CO-NR$^4$R$^5$ wherein Alk, $R^4$ and $R^5$ are as defined herein; and X is oxa or thia; with the proviso that when $R^7$ is a radical of formula CO—NR$^4$R$^5$ or Alk-CO-NR$^4$R$^5$ in which Alk, $R^4$ and $R^5$ are as defined herein then $R^8$ is lower alkyl.

11. A compound of formula VIII

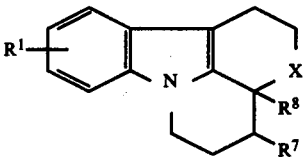

(VIII)

in which $R^1$ is hydrogen; $R^7$ is hydrogen or a radical of formula CO—NR$^4$R$^5$ wherein $R^4$ and $R^5$ each is hydrogen or lower alkyl or Alk—CO—NR$^4$R$^5$ wherein Alk is a straight or branched chain lower alkylene having one to six carbon atoms and $R^4$ and $R^5$ are as defined herein; $R^8$ is lower alkyl or a radical of formula CO—NR$^4$R$^5$ wherein $R^4$ and $R^5$ are as defined herein or Alk—CO—NR$^4$R$^5$ wherein Alk, $R^4$ and $R^5$ are as defined herein; and X is oxa; with the proviso that when $R^7$ is a radical of formula CO—NR$^4$R$^5$ or Alk—CO—NR$^4$R$^5$ in which Alk, $R^4$ and $R^5$ are as defined herein then $R^8$ is lower alkyl.

* * * * *